United States Patent [19]

Matsui et al.

[11] 4,440,928
[45] Apr. 3, 1984

[54] PROCESS FOR PREPARATION OF URACILS

[75] Inventors: Kanenobu Matsui; Shinichiro Uchiumi; Hideki Asada; Takashi Umezu, all of Ube, Japan

[73] Assignee: Ube Industries, Ltd., Yamaguchi, Japan

[21] Appl. No.: 411,464

[22] Filed: Aug. 25, 1982

[30] Foreign Application Priority Data

Sep. 1, 1981 [JP] Japan .................................. 56-136145

[51] Int. Cl.$^3$ ............................................. C07D 239/55
[52] U.S. Cl. ....................................... 544/309; 564/44; 564/45
[58] Field of Search ...................... 544/309; 564/44, 45

[56] References Cited

U.S. PATENT DOCUMENTS 4,239,888 12/1980 Miller .................................. 544/309

FOREIGN PATENT DOCUMENTS 56-86172 7/1981 Japan .................................. 544/309

OTHER PUBLICATIONS

Shaw et al., J. Chem. Soc., 1958, pp. 157–161.
Dewar et al., J. Chem. Soc., 1962, pp. 583–585.

*Primary Examiner*—Paul M. Coughlan, Jr.
*Attorney, Agent, or Firm*—Burgess, Ryan & Wayne

[57] ABSTRACT

Uracil or 5-alkyluracil is prepared by a process wherein a 3,3-dialkoxypropionic acid ester of the formula:

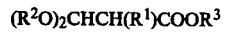

$(R^2O)_2CHCH(R^1)COOR^3$ wherein $R^1$=H or ($C_{1-6}$) alkyl, and $R^2$ and $R^3$ are ($C_{1-8}$) alkyl or ($C_{7-9}$) aralkyl, is reacted with urea in liquid ammonia in the presence of an alkali metal amide, and then, the reaction product is cyclized in the presence of an acid catalyst.

10 Claims, No Drawings

PROCESS FOR PREPARATION OF URACILS

BACKGROUND OF THE INVENTION

(1) Field of the Invention

This invention relates to a process for the preparation of uracils. More specifically, it relates to a process for the preparation of uracil and 5-alkyluracils.

(2) Description of the Prior Art

Uracils are important constituents of nucleic acids and are valuable as starting compounds for the preparation of medicines. 5-Methyluracil, which is one of 5-alkyluracils, is called "thymine" and is an important constituent of nucleic acids. Furthermore, thymine and other 5-alkyluracils are important as starting materials for the preparation of medicines. For example, when uracil is fluorinated, 5-fluorouracil (hereinafter referred to as "5-FU") having a carcinostatic action can be obtained, and it is well known that "Futoraful," which is a famous carcinostatic agent, can be prepared by using 5-FU as a starting material. It is also known that Idoxuridine, which is a famous antiviral agent, is prepared by using uracil as a starting compound.

Since uracil is valuable as a starting material for the preparation of various medicines as described above, various investigations have been made on the process for preparing uracil. As one known process for the preparation of uracil, the process disclosed in Tetrahedron Letters, 27, 2321–2322 (1976), which comprises heating and reacting propiolic acid (CH≡CCOOH) with urea in polyphosphoric acid to form uracil can be mentioned. However, the carboxylic acid used as the starting material is expensive and since the addition of water to the liquid reaction mixture after completion of the reaction is necessary to precipitate uracil, polyphosphoric acid used in a large quantity is difficult to recover for repeated use thereof.

Another known process for the preparation of uracil is the process disclosed in Trans. Science Soc. China, 8, 83–84 (1934), which comprises reacting malic acid with urea in a large quantity of fuming sulfuric acid. This process, however, is defective in that a large quantity of fuming sulfuric acid should be used and since the addition of a large amount of water to the liquid reaction mixture after completion of the reaction is necessary to precipitate uracil, urea and fuming sulfuric acid used for the reaction are difficult to recover for repeated use thereof.

Many processes for the preparation of uracil, other than those mentioned above, are known, but these processes are not satisfactory in that expensive starting materials should be used or the steps are complicated.

SUMMARY OF THE INVENTION

It is a primary object of the present invention to provide a process for the preparation of uracil which is more advantageous in various points than the above-mentioned known processes. Another object of the present invention is to provide a process for preparing a 5-alkyluracil such as thymine according to similar advantageous procedures.

More specifically, in accordance with one aspect of the present invention, a process is provided for the preparation of uracils represented by the following general formula (II):

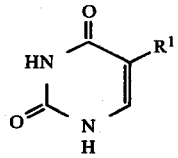

wherein $R^1$ stands for a hydrogen atom or an alkyl group having 1 to 6 carbon atoms,
which comprises reacting a 3,3-dialkoxypropionic acid ester represented by the following general formula (I):

$$(R^2O)_2CHCHCOOR^3 \quad \text{with } R^1 \text{ substituent} \quad (I)$$

wherein $R^1$ is as defined above, and $R^2$ and $R^3$ independently stand for an alkyl group having 1 to 8 carbon atoms or an aralkyl group having 7 to 9 carbon atoms, with urea in liquid ammonia in the presence of an alkali metal amide, and cyclizing the reaction product in the presence of an acid catalyst.

In accordance with another aspect of the present invention, a process is provided for the preparation of uracils represented by the above general formula (II), which comprises cyclizing a 3,3-dialkoxypropionic acid derivative represented by the following general formula (III):

$$(R^2O)_2CHCHCONHCONH_2 \quad \text{with } R^1 \text{ substituent} \quad (III)$$

wherein $R^1$ and $R^2$ are as defined above, in the presence of an acid catalyst.

DESCRIPTION OF THE PREFERRED EMBODIMENTS

According to the process of the present invention, uracils can be prepared in relatively simple reaction steps by using as the starting material a 3,3-dialkoxypropionic acid ester or its derivative, which is inexpensive and readily available. Furthermore, the solvent used for the reaction can easily be recovered and used repeatedly. Accordingly, the process of the present invention is advantageous as an industrial process for the preparation of uracils.

In the process of the present invention, a 3,3-dialkoxypropionic acid ester represented by the following general formula (I):

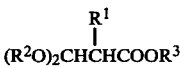

$$(R^2O)_2CHCHCOOR^3 \quad \text{with } R^1 \text{ substituent} \quad (I)$$

is used as the starting material.

In the general formula (I), $R^1$ stands for a hydrogen atom or an alkyl group having 1 to 6 carbon atoms. The alkyl group includes, for example, methyl, ethyl, n-propyl, isopropyl, n-butyl, isobutyl, sec-butyl, tert-butyl, n-pentyl, isopentyl, n-hexyl, and isohexyl groups. Of these, a hydrogen atom and a methyl group are especially preferred.

In the general formula (I), $R^2$ stands for an alkyl group having 1 to 8 carbon atoms or an aralkyl group having 7 to 9 carbon atoms. As the alkyl group, for example, methyl, ethyl, n-propyl, isopropyl, n-butyl, isobutyl, sec-butyl, tert-butyl, n-pentyl, isopentyl, n-hexyl, isohexyl, n-heptyl, n-octyl and 2-ethylhexyl groups can be mentioned. As the aralkyl group, for example, benzyl, phenylethyl and phenylpropyl groups can be mentioned. These alkyl and aralkyl groups may have substituents, so far as the reaction of the process of the present invention is not banefully influenced by these substituents. An alkyl group having 1 to 6 carbon atoms is especially preferred as $R^2$. Ordinarily, the two $R^2$ groups contained in one molecule of the compound of the general formula (I) are the same as each other, but they may be different from each other.

In the general formula (I), $R^3$ stands for an alkyl group having 1 to 8 carbon atoms or an aralkyl group having 7 to 9 carbon atoms. As the group $R^3$, alkyl and aralkyl groups exemplified above with respect to the group $R^2$ can be mentioned. The groups $R^2$ and $R^3$ contained in one molecule of the compound of the general formula (I) may be the same or different.

As examples of the 3,3-dialkoxypropionic acid ester represented by the general formula (I), the following compounds can be mentioned.

(1) Methyl 3,3-dimethoxypropionate, ethyl 3,3-diethoxypropionate, n-propyl 3,3-di-n-propoxypropionate, isopropyl 3,3-diisopropoxypropionate, n-butyl 3,3-di-n-butoxypropionate, isobutyl 3,3-di-isobutoxypropionate, sec-butyl 3,3-di-sec-butoxypropionate, tert-butyl 3,3-di-tert-butoxypropionate, n-pentyl 3,3-di-n-pentylpropionate, isopentyl 3,3-diisopentylpropionate, n-hexyl 3,3-di-n-hexylpropionate, isohexyl 3,3-diisohexylpropionate, n-heptyl 3,3-di-n-heptylpropionate, isoheptyl 3,3-diisoheptylpropionate, n-octyl 3,3-di-n-octylpropionate and 2-ethylhexyl 3,3-di-2-ethylhexylpropionate; and, (2) Methyl 3,3-dimethoxy-2-methylpropionate, ethyl 3,3-diethoxy-2-methylpropionate and n-propyl 3,3-di-n-propoxy-2-methylpropionate.

Furthermore, compounds having substituents such as methyl, ethyl, n-propyl, isopropyl, n-butyl and isobutyl groups at the 2-positions in the propionyl moieties of the compounds listed in (1) above can be mentioned.

The 3,3-dialkoxypropionic acid ester represented by the general formula (I) is a known compound and various processes for the preparation thereof are known. For example, a process can be mentioned wherein methyl acrylate is oxidized in an alcohol solvent in the presence of a $PdCl_2$-$CuCl_2$ catalyst.

In the process of the present invention, the 3,3-dialkoxypropionic acid ester of the general formula (I) is reacted with urea in liquid ammonia in the presence of an alkali metal amide.

It is presumed that this reaction is advanced according to the following reaction formula:

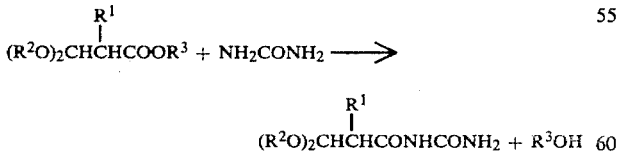

Namely, in the above reaction, 3,3-dialkoxypropionic acid ester is reacted with urea at a molar ratio of 1/1. Accordingly, in carrying out this reaction, urea is ordinarily used in an amount of 0.8 to 2 moles, preferably 1.0 to 1.5 moles, per mole of the 3,3-dialkoxypropionic acid ester. When urea is used in an amount smaller than 0.8 mole or larger than 2 molar per mole of the 3,3-dialkoxypropionic acid ester, the above reaction is advanced, but in the former case, the yield of the intended product is reduced, and in the latter case urea and the alkali metal amide are consumed in undesirably large amounts.

As the alkali metal amide used for the above reaction, sodium amide, potassium amide, and lithium amide can be mentioned. These alkali metal amides are formed when alkali metals are incorporated in liquid ammonia. Accordingly, the alkali metal amide can be introduced into the reaction system by adding an alkali metal such as sodium, potassium or lithium to the liquid ammonia reaction medium. Alternatively, an alkali metal amide prepared separately may be introduced into the reaction system.

If an alkali metal is incorporated in liquid ammonia, hydrogen gas is produced by the alkali metal amide-forming reaction. Accordingly, in view of safety, it is preferable that the incorporation of the alkali metal into liquid ammonia be carried out in an atmosphere of an inert gas such as nitrogen gas or carbon dioxide gas. Since the alkali metal amide is hydrolyzed on contact with water, it is preferable that the water content in each of the substances constituting the reaction system, such as liquid ammonia, be as low as possible.

Ordinarily, the alkali metal amide is used in an equimolar amount to that of urea.

It is preferable that liquid ammonia as the reaction solvent be used in an amount such that the concentration of urea introduced into the reaction system is not more than 20% (weight/volume). If the urea concentration is liquid ammonia is too high, that is, if the amount of liquid ammonia used is too small, the yield of the intended product is reduced.

This reaction is ordinarily accomplished by dropping the 3,3-dialkoxypropionic acid ester into liquid ammonia in which urea and the alkali metal amide have been dissolved.

It is preferable that the reaction of the 3,3-dialkoxypropionic acid ester with urea be carried out at a temperature of from $-70°$ C. to $+10°$ C. Even if the temperature is lower than $-70°$ C., the reaction is advanced and a good yield is obtained, but since the reaction system should be maintained under cooling, the process becomes disadvantageous from the industrial viewpoint. If the reaction temperature is higher than $+10°$ C., a pressure device or the like is necessary for keeping ammonia as the reaction medium in the liquid state, and the process becomes disadvantageous from the industrial viewpoint.

The reaction of the 3,3-dialkoxypropionic acid ester with urea is ordinarily completed within 10 minutes, though the reaction time varies depending upon the reaction temperature and the concentrations of the starting materials.

By the above reaction, 3,3-dialkoxypropionic acid derivatives having the following general formula (III):

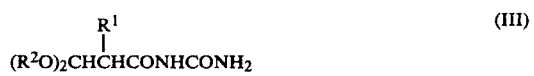

are obtained. In the general formula (III), $R^1$ and $R^2$ are the same groups as $R^1$ and $R^2$ of the 3,3-dialkoxypropionic acid ester of the general formula (I) used as the starting material.

The 3,3-dialkoxypropionic acid derivative may be used for the subsequent reaction step (cyclization step) after isolation from the reaction mixture, or the residue left after only liquid ammonia is removed from the reaction mixture may be fed to the subsequent cyclization step without particular isolation of the 3,3-dialkoxypropionic acid derivative. As the method separating the 3,3-dialkoxypropionic acid derivative from liquid ammonia, a method can be adopted in which ammonia is volatilized after completion of the reaction and a method in which the precipitate (containing the above derivative) formed in the reaction mixture is recovered by filtration. If necessary, the so-obtained residue or precipitate containing the 3,3-dialkoxypropionic acid derivative may be isolated and purified by neutralizing, washing, and crystallization.

Cyclization of the 3,3-dialkoxypropionic acid derivative having the general formula (III) is carried out in the presence of an acid catalyst, ordinarily in a solvent. When the above-mentioned residue or unrefined precipitate of the reaction product is used as the 3,3-dialkoxypropionic acid derivative, it is preferable that the alkali component contained in the residue or precipitate be neutralized with an inorganic acid such as sulfuric acid, hydrochloric acid, or phosphoric acid, or an organic acid such as acetic acid or formic acid before the residue or precipitate is introduced into the cyclization reaction system. If the above-mentioned residue or precipitate is introduced into the cyclization reaction system without this neutralization step, when the amount of the acid catalyst to be used at the cyclization step is determined, the amount necessary for neutralizing the alkali component should be taken into account.

It is preferable that a strong acid be used as the acid catalyst. As the strong acid, for example, inorganic acids such as sulfuric acid, hydrochloric acid, and phosphoric acid, and organic acids such as p-toluenesulfonic acid, benzenesulfonic acid, and trichloroacetic acid can be mentioned. The acid catalyst is used in an amount of 0.001 to 0.1 mole per gram of the 3,3-dialkoxypropionic acid derivative, and the concentration of the acid catalyst in the reaction system is adjusted to at least 0.1% by weight.

Any solvents capable of dissolving therein the 3,3-dialkoxypropionic acid derivative can be used at the cyclization step. Preferable examples of the solvent include, aliphatic alcohols such as methanol, ethanol, n-propanol, isopropanol, butanol, pentanol and hexanol, and water, dimethylformamide, dimethylsulfone and dimethylsulfoxide. These solvents may be used alone or in combination. It is sufficient if the solvent is used in an amount large enough to dissolve the 3,3-dialkoxypropionic acid derivative or the residue or precipitate containing this derivative, but ordinarily, the solvent is used in an amount at least 10 times the amount of the derivative or the residue or precipitate based on the weight.

The cyclization reaction is carried out at a reaction temperature of 20° C. to 150° C., preferably 50° C. to 120° C. Too low a reaction temperature is not recommended because if the reaction temperature is too low, the rate of reaction is low. If the reaction temperature is higher than 150° C., the 3,3-dialkoxypropionic acid derivative produced is liable to be decomposed. Ordinarily, the reaction time is 0.5 to 5 hours, though the preferable reaction time varies to some extent depending upon the reaction temperature, the particular reactant and its concentration, and the particular catalyst.

After completion of the cyclization reaction, the formed uracils are precipitated, and this precipitate can be recovered by filtration. If necessary, the precipitate is purified. Thus, the intended uracils can be obtained at a high purity. A small amount of uracils are left in the state dissolved in the filtrate left after recovery of the uracils by filtration. Accordingly, this filtrate can advantageously be recycled to the cyclization step for use as the reaction medium.

The uracils obtained by the cyclization reaction are compounds represented by the following general formula (II):

In the above general formula (II), the group $R^1$ is the same as $R^1$ of the 3,3-dialkoxypropionic acid ester of the general formula (I) or the 3,3-dialkoxypropionic acid derivative of the general formula (III), which has been used as the starting material.

The present invention will now be described in detail with reference to the following examples.

EXAMPLE 1

A 50-ml capacity three-neck flask equipped with a dropping funnel and a tube for potassium hydroxide for drying was charged with 1.50 g of completely dried urea, and the flask was cooled by immersing the flask in a dry ice-acetone thermostat tank maintained at a temperature of about −68° C.

After the flask was sufficiently cooled, ammonia gas was introduced into the flask from an ammonia bomb to charge the flask with 20 ml of liquid ammonia. Then, 0.57 g of metallic sodium was added to liquid ammonia whereby metallic sodium was immediately dissolved therein to form a liquid ammonia solution having a deep blue color.

Then, 3.91 g of methyl 3,3-dimethoxypropionate was dropped through the dropping funnel over a period of about 5 minutes, and for about 30 minutes from the point of completion of the dropwise addition, the reaction was conducted while the reaction mixture was stirred occasionally and cooled in the dry ice-acetone thermostat tank.

After completion of the reaction, the flask was taken out from the thermostat tank and allowed to stand still at room temperature, whereby ammonia was vaporized and a residue was obtained. This residue was dissolved in 5 ml of water, and 2 ml of acetic acid was added to the solution to effect neutralization.

To the neutralized solution 5 ml of water, 30 ml of methanol and 1 ml of an aqueous 35% solution of hydrochloric acid were added, and the mixture was heated under reflux for 3.5 hours. After completion of the reaction, the liquid reaction mixture was cooled to room temperature, and the formed precipitate was recovered by filtration to obtain 1.35 g of the precipitate. The IR spectrum and NMR spectrum of the obtained precipitate were the same as those of uracil. The yield was 47% (based on methyl 3,3-dimethoxypropionate).

EXAMPLE 2

The procedure of Example 1 was repeated in the same manner as in Example 1 except that the amount of liquid ammonia introduced into the flask was changed to 40 ml, whereby 1.89 g of uracil was obtained. The yield was 64% (on the same basis as in Example 1).

EXAMPLE 3

The procedure of Example 1 was repeated in the same manner as in Example 1 except that the amount of liquid ammonia introduced into the flask was changed to 40 ml, 4.1 g of ethyl 3,3-diethoxy-2-methylpropionate was used instead of methyl 3,3-dimethoxypropionate, and the same amount of ethanol was used instead of methanol, whereby 0.92 g of thymine was obtained. Identification of thymine was performed by IR spectrum and NMR spectrum as in Example 1. The yield was 34% (based on ethyl 3,3-diethoxy-2-methylpropionate).

EXAMPLE 4

According to the procedures described in Example 1, 3.9 g of methyl 3,3-dimethoxypropionate was reacted with 1.50 g of urea in liquid ammonia, and then, ammonia was vaporized to obtain a residue.

When 20 ml of water was added to the residue at room temperature and 2 ml of acetic acid was then added, a light yellow precipitate was obtained. The precipitate was recovered by filtration, washed with about 40 ml of ether and dried to obtain 3.5 g of a crystal having a melting point of 163° C. to 165° C. From data of NMR spectrum, IR spectrum, and mass spectrum, the crystal was identified as a compound having the formula $(CH_3O)_2CHCH_2CONHCONH_2$ (hereinafter, this compound will be referred to as "intermediate"). The yield was 75% (based on methyl 3,3-dimethoxypropionate).

Then, 0.5 g of the intermediate was added to a mixture comprising 5 ml of water, 15 ml of methanol, and 1 ml of an aqueous 35% hydrochloric acid solution, and the mixture was heated under reflux for 3.5 hours. After completion of the reaction, the reaction mixture liquid was cooled to room temperature and the formed precipitate was recovered by filtration to obtain 0.14 g of uracil. The yield was 44% based on the intermediate and 34% based on methyl 3,3-dimethoxypropionate.

EXAMPLE 5

Heating under reflux (cyclization reaction) was carried out by using 0.5 g of the intermediate obtained in Example 4 under the same conditions as in Example 4 except that 2 ml of concentrated sulfuric acid was used instead of 1 ml of the aqueous 35% hydrochloric acid solution, whereby 0.11 g of uracil was obtained. The yield was 35% (based on the intermediate).

EXAMPLE 6

The procedure of Example 4 was repeated in the same manner as in Example 4 except that the amounts of liquid ammonia and urea were changed to 25 ml and 3.0 g, respectively, whereby 2.2 g of the intermediate was obtained. The yield of the intermediate was 48% (based on methyl 3,3-dimethoxypropionate). The NMR spectrum and IR spectrum of the so-obtained intermediate were the same as those of the intermediate obtained in Example 4.

Under the same conditions as described in Example 4, 1.5 g of the intermediate was heated under reflux in a mixture comprising 20 ml of water and 2 ml of an aqueous 35% hydrochloric acid solution, whereby 0.40 g of uracil was obtained. The yield was 42% (based on the intermediate).

EXAMPLE 7

According to the procedure described in Example 1, 3.91 g of methyl 3,3-dimethoxypropionate was reacted with 1.50 g of urea in liquid ammonia, and ammonia was vaporized to obtain a residue. Then, 20 ml of methanol and 5 g of p-toluenesulfonic acid were added to the residue, and the mixture was heated under reflux in the same manner as described in Example 1, whereby 0.47 g of uracil was obtained. The yield was 21% (based on methyl 3,3-dimethoxypropionate).

EXAMPLE 8

In the same manner as described in Example 1, the reaction was carried out in 40 ml of liquid ammonia by using 5.0 g of n-butyl 3,3-di-n-butoxypropionate, 1.50 g of urea and 0.64 g of metallic potassium.

Ammonia was vaporized from the reaction mixture at room temperature, and 30 ml of butanol and 2.5 ml of an aqueous 35% hydrochloric acid solution were added to the obtained residue and the mixture was stirred for 2 hours in a thermostat tank maintained at 90° C. to effect reaction. The liquid reaction mixture was cooled to room temperature to obtain 0.96 g of uracil. The yield was 52% (based on n-butyl 3,3-di-n-butoxypropionate).

EXAMPLE 9

The procedure of Example 1 was repeated in the same manner except that 0.57 g of lithium amide was used instead of metallic sodium, whereby 1.25 g of uracil was obtained. The yield was 56% (on the same basis as in Example 1).

We claim:

1. A process for the preparation of uracils represented by the formula:

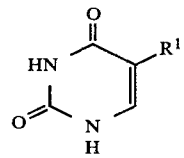

wherein $R^1$ stands for a hydrogen atom or an alkyl group having 1 to 6 carbon atoms,
which comprises reacting a 3,3-dialkoxypropionic acid ester represented by the formula:

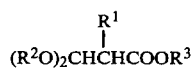

wherein $R^1$ is as defined above, and $R^2$ and $R^3$ independently stand for an alkyl group having 1 to 8 carbon atoms or an aralkyl group having 7 to 9 carbon atoms, with urea in liquid ammonia in the presence of an alkali metal amide, and cyclizing the reaction product in the presence of an acid catalyst.

2. A process for the preparation of uracils represented by the formula:

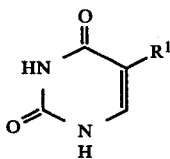

wherein R[1] stands for a hydrogen atom or an alkyl group having 1 to 6 carbon atoms,
which comprises cyclizing a 3,3-dialkoxypropionic acid derivative represented by the formula:

wherein R[1] is as defined above, and R[2] independently stand for an alkyl group having 1 to 8 carbon atoms or an aralkyl group having 7 to 9 carbon atoms,
in the presence of an acid catalyst.

3. A process according to claim 1 or 2 wherein R[1] is a hydrogen atom or a methyl group and R[2] is an alkyl group having 1 to 6 carbon atoms.

4. A process according to claim 1 wherein the amount of urea used is in the range of from 0.8 to 2.0 moles per mole of the 3,3-dialkoxypropionic acid ester.

5. A process according to claim 1 wherein the alkali amide is selected from the group consisting of sodium amide, potassium amide, and lithium amide.

6. A process according to claim 1 wherein the amount of liquid ammonia used is such that the concentration of urea present in the reaction system is not more than 20 weight/volume %.

7. A process according to claim 1 wherein the 3,3-dialkoxypropionic acid ester is reacted with urea at a temperature of from $-70°$ C. to $+10°$ C.

8. A process according to claim 1 or 2 wherein the acid catalyst is selected from the group consisting of sulfuric acid, hydrochloric acid, phosphoric acid, p-toluenesulfonic acid, benzenesulfonic acid, and trichloroacetic acid and used in an amount of 0.001 to 0.1 mole per gram of the 3,3-dialkoxypropionic acid derivative.

9. A process according to claim 1 or 2 wherein the cyclization reaction is carried out in a solvent capable of dissolving therein the 3,3-dialkoxypropionic acid derivative.

10. A process according to claim 1 or 2 wherein the cyclization reaction is carried out at a temperature of from 20° C. to 150° C.

* * * * *